(12) United States Patent
Joshi et al.

(10) Patent No.: US 7,822,253 B2
(45) Date of Patent: Oct. 26, 2010

(54) METHODS AND APPARATUS FOR BMD MEASURING

(75) Inventors: Mukta Chandrashekhar Joshi, Belmont, MA (US); Thomas Louis Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1053 days.

(21) Appl. No.: 11/485,136

(22) Filed: Jul. 12, 2006

(65) Prior Publication Data

US 2008/0013813 A1 Jan. 17, 2008

(51) Int. Cl.
*G06K 9/00* (2006.01)
(52) U.S. Cl. ..................................... 382/131
(58) Field of Classification Search ............ 378/4, 378/8, 901, 18, 19, 21, 23; 382/128, 130, 382/131, 132, 100; 600/407, 425; 128/920
See application file for complete search history.

(56) References Cited

U.S. PATENT DOCUMENTS

| | | | | |
|---|---|---|---|---|
| 4,922,915 A * | 5/1990 | Arnold et al. | ............... | 382/128 |
| 5,068,788 A * | 11/1991 | Goodenough et al. | ....... | 382/131 |
| 5,138,553 A * | 8/1992 | Lanza et al. | ................. | 600/407 |
| 5,577,089 A * | 11/1996 | Mazess | ....................... | 378/54 |
| 5,687,210 A * | 11/1997 | Maitrejean et al. | ............ | 378/57 |
| 5,772,592 A * | 6/1998 | Cheng et al. | ................. | 600/407 |
| 5,852,647 A * | 12/1998 | Schick et al. | ................. | 378/53 |
| 5,915,036 A * | 6/1999 | Grunkin et al. | ............. | 382/132 |
| 6,246,745 B1 * | 6/2001 | Bi et al. | ......................... | 378/54 |
| 2003/0095695 A1 * | 5/2003 | Arnold | ........................ | 382/131 |
| 2004/0101104 A1 * | 5/2004 | Avinash et al. | ........... | 378/98.12 |
| 2005/0094859 A1 * | 5/2005 | Ruth et al. | ................... | 382/132 |
| 2005/0283072 A1 * | 12/2005 | Qin et al. | ..................... | 600/437 |
| 2006/0074288 A1 * | 4/2006 | Kelly et al. | ................. | 600/407 |
| 2007/0253529 A1 * | 11/2007 | Seppi | .......................... | 378/21 |

OTHER PUBLICATIONS

Nikoloff et al., "Bone Mineral Assessment: New Dual-Energy CT Approach", Radiology 1988; 168:223-228.*
Yuasa et al., "Reconstruction method for fluorescent x-ray computed tomography by least-squares method using singular decomposition", IEEE Transactions on Nuclear Science, vol. 44, No. 1, Feb. 1997, p. 54-62.*
Image Analysis, Inc. @ www.image-analysis.com/indxtxt.htm; Jul. 12, 2006; 1 page, The Leader in QCT Bone Densitometry.
Fluke Biomedical @ www.flukebiomedical.com/RMS/productDataSheets/BoneDensitySoftware-ds.pdf; 2 pages; PC/QCT Bone Mineral Density Software Model 49-800, Printed Feb. 26, 2005.

* cited by examiner

*Primary Examiner*—Andrew W Johns
*Assistant Examiner*—Tahmina Ansari
(74) *Attorney, Agent, or Firm*—ZPS Group, SC

(57) ABSTRACT

A method includes scanning a patient without a BMD reference present to obtain data, and performing a BMD analysis on the obtained data.

20 Claims, 5 Drawing Sheets

Fitting the BMD reference to patient data

Figure 3 – Patient Image with BMD Reference phantom
Figure 4 – Image projection Area (summation of pixel values times the pixel size)
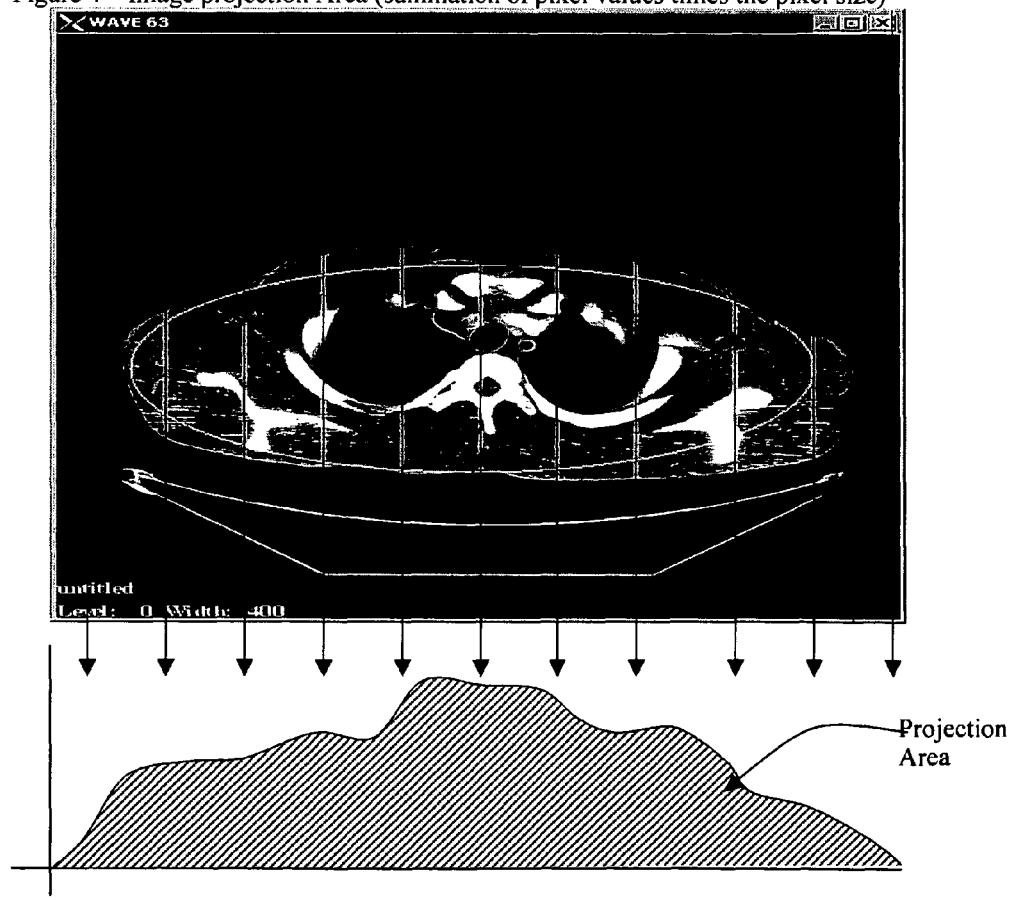

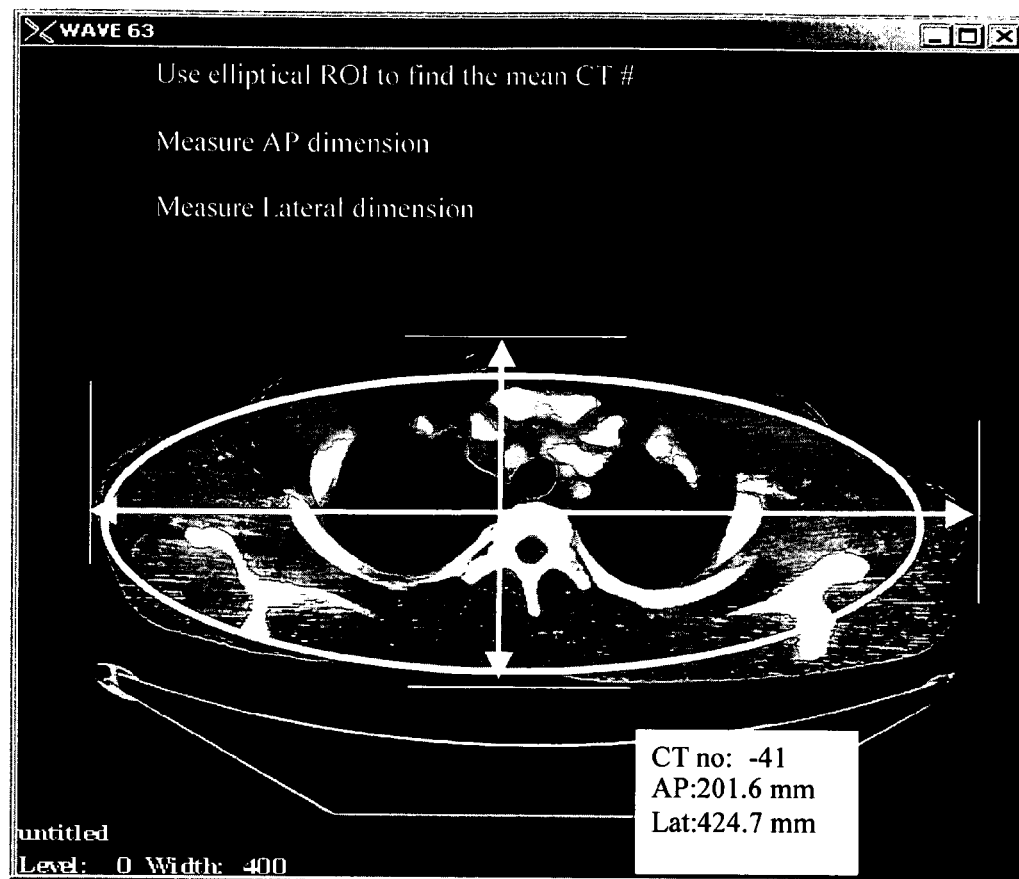
Figure 5 An alternative way to compute the Image Projection Area using ROI and distance measurements

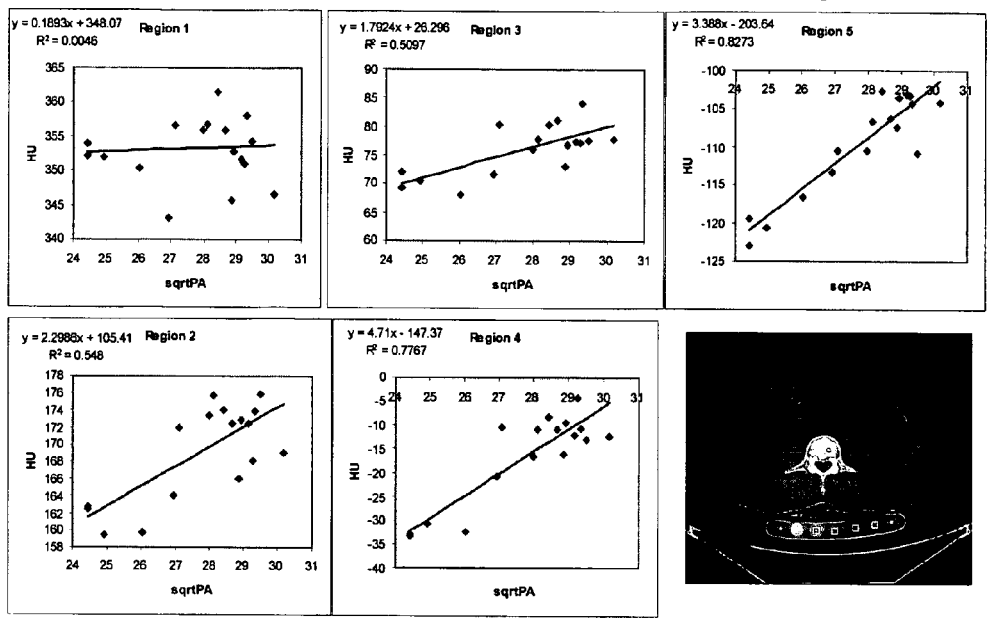
Figure 6 Fitting the BMD reference to patient data

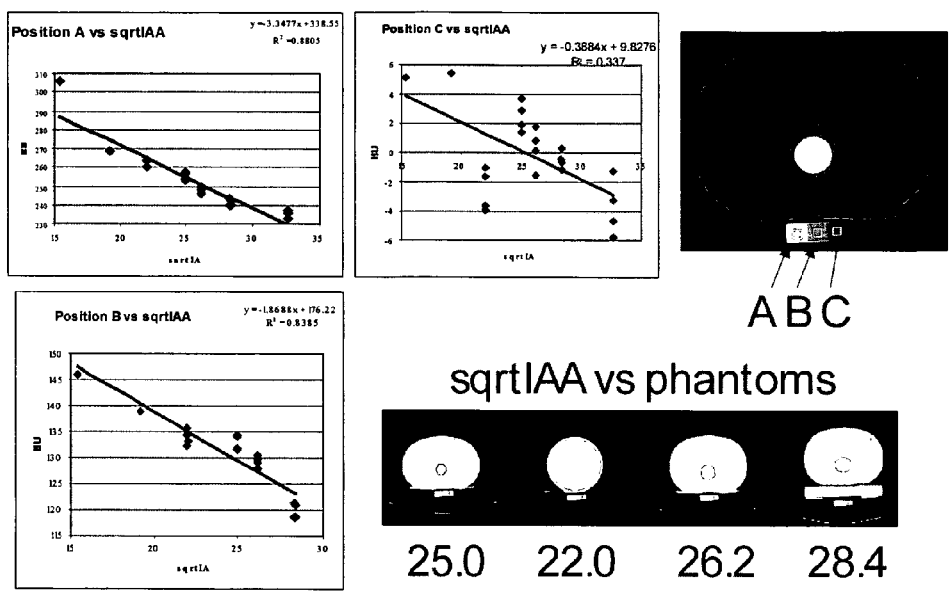
Figure 7 – fitting the BMD reference data to phantom data

METHODS AND APPARATUS FOR BMD MEASURING

BACKGROUND OF THE INVENTION

This invention relates generally to Diagnostic Imaging (DI) measurements, and, more particularly, to Bone Mineral Density (BMD) measurements which are the measurements of the amount of bone mineral per unit volume of bone tissue.

The accurate measurement of bone density with Computed Tomography (CT) requires a BMD reference phantom (generally solid Calcium Hydroxyapatite) to be scanned along with the patient scan such that the phantom appears in all the desired patient images. This is required since CT number values for human tissue (especially bone) change as a function of the size of the patient section and the amount of bone, fat, muscle, etc in the scan section. The reference phantom's CT values are affected similarly by the patient's characteristics. Thus, changes in the reference phantom values can be used to calibrate CT number readings from the patient's bone in order to calculate a more accurate BMD value. This is often done using commercial software products such as the QCT-3000 System commercially available from Image Analysis, Inc. of Columbia, Ky.

Most patient CT scans are prescribed for reasons other then BMD screening. It would however be useful to identify patients who are at risk for osteoporosis for follow-up study using information from a routine CT scan (i.e., not a specifically prescribed BMD scan). Specifically, this would require that a BMD estimate could be made with reasonable first order accuracy from bone Region Of Interest (ROI) measurements without the use of a BMD reference phantom.

BRIEF DESCRIPTION OF THE INVENTION

In one aspect, a method includes scanning a patient without a BMD reference present to obtain data, and performing a BMD analysis on the obtained data.

In another aspect, a computer readable medium is embedded with a program configured to instruct a computer to perform a BMD analysis on scan data that does not include BMD phantom data.

In still another aspect, a system I provided. The system includes a radiation source, a detector positioned to receive radiation emitted from the source, and a computer operationally coupled to the source and the detector. The computer is configured to perform a BMD analysis on scan data that does not include BMD phantom data.

BRIEF DESCRIPTION OF THE DRAWINGS

FIG. 3 illustrates a patient image with a BMD reference phantom.

FIG. 4 illustrates an Image projection Area (summation of pixel values times the pixel size).

FIG. 5 illustrates an alternative way to compute the Image Projection Area using ROI and distance measurements.

FIG. 6 illustrates fitting the BMD reference to patient data.

FIG. 7 illustrates fitting the BMD reference data to phantom data.

DETAILED DESCRIPTION OF THE INVENTION

Figure 1:
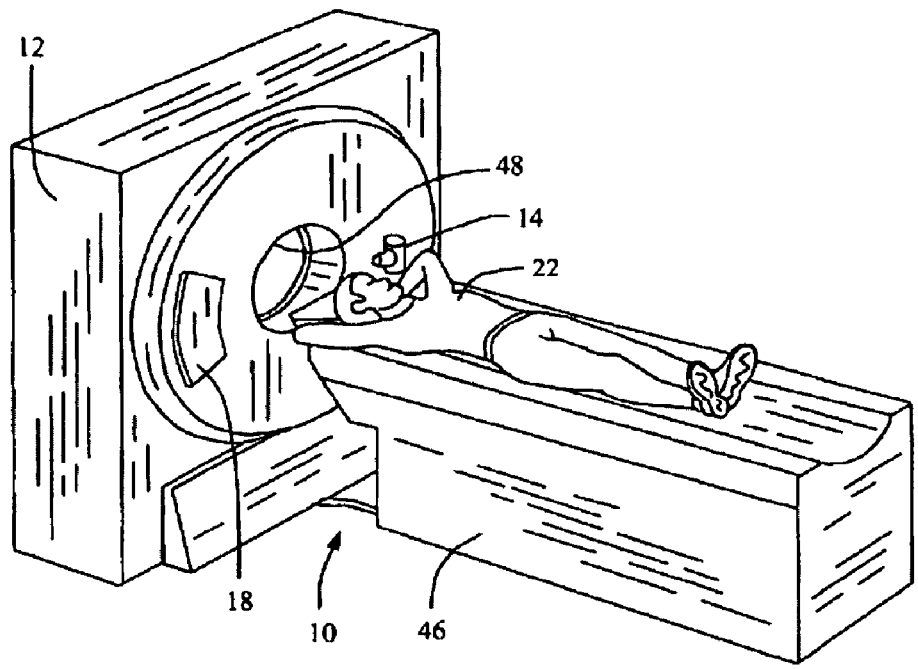
FIG. 1 is a pictorial view of a CT imaging system embodiment.

There are herein described BMD measurement methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of CT, it is contemplated that the benefits of the invention accrue to all system with x-ray tubes such as a combined PET/CT system or an x-ray system, and in one embodiment, the system below is a combined PET/CT system, which is of course a CT capable system. Additionally, it is contemplated that the benefits of the invention accrue to all diagnostic imaging (DI) modalities including PET, MRI, and Ultrasound, for example, and therefore as used herein the terms "radiation source" and "detector" are meant to be broad and include such modalities.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units (HU)", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
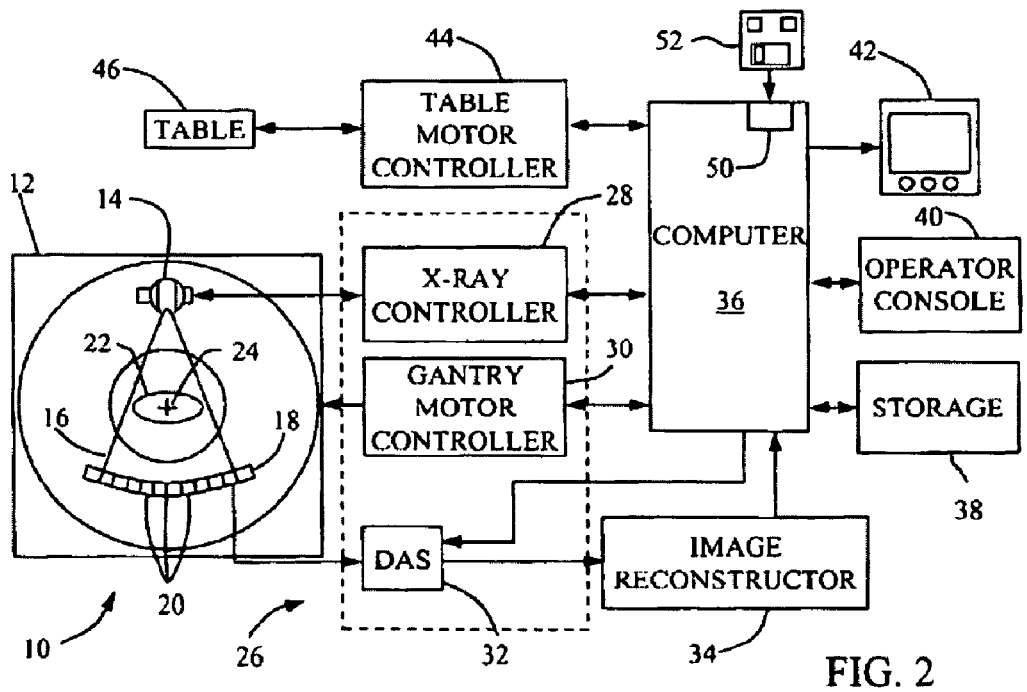
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

Patient characteristics that affect x-ray attenuation can be related to the square root of the image attenuation area (sqrtIAA). The attenuation area can be determined from an image in several ways as shown in FIG. 4 & FIG. 5. In FIG. 4 the IAA is calculated as the sum of the image pixel values multiplied by the pixel size. In FIG. 5, the IAA is estimated as $\pi/2 \times AP \times L \times CT$ (where AP is the vertical distance, L is the Lateral distance and CT is the mean CT number of the overall patient region). For FIG. 5, an elliptical ROI was used to find the mean CT number. Care was taken not to include too much background or to exclude too much bone. For the AP and L, care was taken to find the true lengths to the maximum outlining points.

In one first order implementation, a reference phantom is scanned along with a set of patients undergoing BMD screening. The BMD reference phantom values are recorded along with the IAA for each patient. The BMD reference values are then fit to the square root of the IAA using a linear regression equation (FIG. 6). As an alternative, the BMD reference values could be scanned using phantoms instead of patients (FIG. 7). Once the regression equation is determined, it is stored for use during routine patient scanning. A patient in the risk group for osteoporosis who is being scanned for other clinical indications could be evaluated for BMD risk. The IAA is calculated for the patient, and estimated BMD reference values are obtained using the regression equation. The appropriate bone measurements and BMD reference values are provided to the BMD computation software for BMD evaluation in the same manner as if an actual BMD reference were used.

In a more refined implementation, a set of tissue specific LAA values could be calculated by thresholding the HU values for specific tissues (gross IAA, bone HU>200, fat between −100 HU and −20, and muscle in the range of 10<HU<40, for examples). To improve accuracy, the BMD reference values could than be fit as a function of overall body size, and the amount of bone, fat, and muscle in the CT scan section.

Technical effects include an accurate automatic method to estimate BMD reference values in order to calculate bone density from routine CT body scan images without the use of a BMD reference phantom. Any inaccuracies of any non phantom calibration methods may be associated with the placement of ROIs to measure tissue specific regions on the patient image and with variations inherent in individual patient anatomy. Therefore, by fitting the BMD reference values as a function of overall body size, and the amount of bone, fat, and muscle in the CT scan section, the resultant images will be more accurate.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A CT system comprising:
   a rotatable gantry having an opening to receive a patient to be scanned;
   a high frequency electromagnetic energy projection source configured to project a high frequency electromagnetic energy beam toward the object;
   a detector array configured to detect high frequency electromagnetic energy passing through the patient;
   a data acquisition system (DAS) connected to the detector array and configured to receive imaging data therefrom, the imaging data being free of a bone mineral density (BMD) reference phantom; and
   a computer programmed to:
      calculate a patient image attenuation area (IAA) from the CT imaging data;
      compare the patient IAA to a plurality of BMD reference values and a plurality of reference IAAs; and
      determine a patient BMD value based on the comparison of the patient IAA to the plurality of BMD reference values and the plurality of reference IAAs.

2. The CT system of claim 1 wherein the computer is further programmed to:
   fit the plurality of BMD reference values to a square root of the plurality of reference IAAs to determine a linear regression equation correlating the plurality of BMD reference values to the plurality of reference IAAs; and
   input the patient IAA to the linear regression equation to determine the patient BMD value.

3. The CT system of claim 2 wherein the computer is further programmed to:
   identify a plurality of specific tissue-types in each of the plurality of reference IAAs;
   determine a tissue IAA for each of the plurality of specific tissue-types in each respective reference IAA;
   assign a Houndsfield unit threshold range to each of the plurality of specific tissue-types; and
   fit the plurality of BMD reference values to the plurality of reference IAAs as a function of the tissue IAA for each of the plurality of specific tissue-types in each respective reference IAA.

4. The CT system of claim 1 wherein the computer is further programmed to calculate the patient IAA as a sum of image pixel values multiplied by a pixel size, the image pixel values and the pixel size being determined from the imaging data.

5. The CT system of claim 1 wherein the computer is further programmed to calculate the patient IAA according to:

$$IAA = \pi/2 * AP * L * CT,$$

wherein AP is a vertical distance, L is a lateral distance, and CT is a mean CT number, as determined from the imaging data.

6. A method for determining bone mineral density (BMD) of a patient from a CT scan free of a BMD reference phantom, the method comprising:
   performing a CT scan on a patient without a BMD reference phantom present to obtain image data;
   calculating an image attenuation area (IAA) of the patient from the image data;
   accessing a lookup table having stored thereon a plurality of BMD reference values correlated with a plurality of IAAs; and
   determining a patient BMD value based on the calculated IAA of the patient and the BMD reference values and IAAs of the lookup table.

7. The method of claim 6 wherein calculating the IAA comprises calculating the IAA as a sum of image pixel values multiplied by a pixel size, the image pixel values and the pixel size being determined from the image data.

8. The method of claim 6 wherein calculating the IAA comprises calculating the IAA as:

$$IAA = \pi/2 * AP * L * CT,$$

wherein AP is a vertical distance, L is a lateral distance, and CT is a mean CT number, as determined from the image data.

9. The method of claim 6 wherein the lookup table comprises a linear regression equation stored thereon, the linear regression equation fitting each of the plurality of BMD reference values to a square root of the IAAs.

10. The method of claim 9 wherein determining the patient BMD value comprises estimating the patient BMD value from the calculated IAA of the patient and the linear regression equation.

11. The method of claim 6 wherein the lookup table comprises a plurality of tissue-specific IAAs, each tissue-specific IAA identifying a plurality of specific tissue-types in an overall IAA, with each specific tissue-type having a specified range of Houndsfield units correlated therewith.

12. The method of claim 11 wherein the lookup table comprises a linear regression equation stored thereon, the linear regression fitting each of the plurality of BMD reference values to a square root of the tissue-specific IAAs, such that the plurality of BMD reference values are fit to the plurality of specific tissue-types in the overall IAA.

13. The method of claim 12 wherein calculating the IAA of the patient comprises calculating a tissue-specific IAA of the patient from the image data; and
   wherein determining the patient BMD value comprises estimating the patient BMD value from the calculated tissue-specific IAA of the patient and the linear regression equation.

14. The method of claim 6 further comprising:
   performing a series of scans on a plurality of reference patients using a BMD reference phantom;
   acquiring a plurality of BMD reference values and a plurality of IAAs from the series of scans; and
   correlating the plurality of BMD reference values to the plurality of IAAs to generate the lookup table.

15. A non-transitory computer readable storage medium having a computer program stored thereon and representing a set of instructions that when executed by a computer causes the computer to: acquire CT imaging data from a beam of high frequency electromagnetic energy attenuated through a patient and detected by a detector array, the CT imaging data being free of a bone mineral density (BMD) reference phantom; calculate an image attenuation area (IAA) of the patient from the CT imaging data; input the IAA of the patient into a linear regression equation, the linear regression equation correlating a plurality of BMD reference values to a plurality of reference IAAs; and determine a patient BMD value based on input of the calculated IAA of the patient into the linear regression equation.

16. The non-transitory computer readable storage medium of claim 15 wherein the computer program further causes the computer to calculate the IAA as a sum of image pixel values multiplied by a pixel size, the image pixel values and the pixel size being determined from the CT imaging data.

17. The non-transitory computer readable storage medium of claim 15 wherein the computer program further causes the computer to calculate the IAA according to:

$$IAA = \pi/2 * AP * L * CT,$$

wherein AP is a vertical distance, L is a lateral distance, and CT is a mean CT number, as determined from the imaging data.

18. The non-transitory computer readable storage medium of claim 15 wherein the computer program further causes the computer to fit the plurality of BMD reference values to a square root of the IAAs to determine the linear regression equation.

19. The non-transitory computer readable storage medium of claim 15 wherein the computer program further causes the computer to: identify a plurality of specific tissue-types in each of the plurality of reference IAAs; determine a tissue IAA for each of the plurality of specific tissue-types in each respective reference IAA; assign a Hounsfield unit threshold range to each of the plurality of specific tissue-types; and fit the plurality of BMD reference values to the plurality of reference IAAs as a function of the tissue IAA for each of the plurality of specific tissue-types in each respective reference IAA.

20. The non-transitory computer readable storage medium of claim 15 wherein the computer program further causes the computer to acquire the plurality of BMD reference values and the plurality of reference IAAs from either a plurality of patient-reference phantom scans or a plurality of reference phantom scans.

* * * * *

UNITED STATES PATENT AND TRADEMARK OFFICE
CERTIFICATE OF CORRECTION

| | | |
|---|---|---|
| PATENT NO. | : 7,822,253 B2 | Page 1 of 1 |
| APPLICATION NO. | : 11/485136 | |
| DATED | : October 26, 2010 | |
| INVENTOR(S) | : Joshi et al. | |

It is certified that error appears in the above-identified patent and that said Letters Patent is hereby corrected as shown below:

Col. 7, line 18 (Claim 17), delete "from the imaging" and substitute therefore -- from the CT imaging --.

Signed and Sealed this
Fourth Day of January, 2011

David J. Kappos
*Director of the United States Patent and Trademark Office*